United States Patent
Matchett

(10) Patent No.: US 7,307,202 B2
(45) Date of Patent: Dec. 11, 2007

(54) TRITICALE CULTIVAR 97TV38011

(75) Inventor: Robert W. Matchett, Zamora, CA (US)

(73) Assignee: Resource Seeds, Inc., Gilroy, CA (US)

( * ) Notice: Subject to any disclaimer, the term of this patent is extended or adjusted under 35 U.S.C. 154(b) by 172 days.

(21) Appl. No.: 11/236,288

(22) Filed: Sep. 27, 2005

(65) Prior Publication Data

US 2007/0074302 A1   Mar. 29, 2007

(51) Int. Cl.
- A01H 5/00 (2006.01)
- A01H 5/10 (2006.01)
- A01H 4/00 (2006.01)
- A01H 1/00 (2006.01)
- C12N 15/82 (2006.01)

(52) U.S. Cl. .............. 800/320; 800/260; 800/278; 800/279; 800/281; 800/298; 800/301; 800/302; 800/300; 435/410

(58) Field of Classification Search .......... 800/260, 800/265, 278, 279, 281, 298, 300, 301, 302, 800/303, 320; 435/410
See application file for complete search history.

(56) References Cited

U.S. PATENT DOCUMENTS 5,523,520 A   6/1996   Hunsperger et al.

OTHER PUBLICATIONS

Plant Variety Protection Certificate No. 9900400, Triticale, 'Triticale 105', granted Jun. 2, 2002.*

Wikipedia, the free encyclopedia, retrieved from "http//en.wikipedia.org/wiki/Triticale" on May 2, 2007, pp. 1-5.*

Allard, R.W., 1960. Selection under self-fertilization. In Principles of Plant Breeding, John Wiley & Sons, Inc., p. 55.

Eshed, et al., 1996. Less-than-additive epistatic interactions of quantitative trait loci in tomato. Genetics 143:1807-1817.

Kraft, et al., 2000. Linkage disequilibrium and fingerprinting in sugar beet. Theor. Appl. Genet. 101:323-326.

Poehlman, J.M. and Sleper, D.A., Methods in Plant Breeding, In Breeding Field Crops, 4th ed. (1995), Iowa State University Press, pp. 172-174.

* cited by examiner

Primary Examiner—David H. Kruse
Assistant Examiner—Keith O. Robinson
(74) Attorney, Agent, or Firm—Jondle & Associates, P.C.

(57) ABSTRACT

A triticale cultivar, designated 97TV38011, is disclosed. The invention relates to the seeds of triticale cultivar 97TV38011, to the plants of triticale 97TV38011, and to methods for producing a triticale plant produced by crossing the cultivar 97TV38011 with itself or another triticale variety. The invention also relates to methods for producing a triticale plant containing in its genetic material one or more transgenes and to the transgenic triticale plants and plant parts produced by those methods. The invention also relates to triticale varieties or breeding varieties and plant parts derived from triticale cultivar 97TV38011, to methods for producing other triticale varieties, lines or plant parts derived from triticale cultivar 97TV38011, and to the triticale plants, varieties, and their parts derived from the use of those methods. The invention further relates to hybrid triticale seeds and plants produced by crossing the cultivar 97TV38011 with another triticale cultivar.

24 Claims, No Drawings

TRITICALE CULTIVAR 97TV38011

BACKGROUND OF THE INVENTION

The present invention relates to a triticale seed, a triticale plant, a triticale cultivar and a triticale hybrid. This invention further relates to a method for producing triticale seed and plants. All publications cited in this application are herein incorporated by reference.

Triticale (*Triticale hexaploide* L.) is a crop species resulting from a cross between wheat (*Triticum*) and rye (*Secale*). It is a man-made crop in that plant breeders must physically make crosses and then manipulate the resultant offspring to obtain a self-fertile plant. Triticales are agronomically desirable due to their ideal combinations of the yield and quality advantages of common wheat, and the hardiness, pest tolerance, and adaptability of rye.

Hybrids of wheat and rye date back to the late 1800's, however early attempts to cross wheat and rye produced only sterile offspring, so for many years triticale was only a scientific novelty. Fertile triticales capable of producing viable seed were virtually unknown until the late 1930's when a Swedish geneticist named Arne Muntzing produced fertile triticale by treating the hybrids with colchicines, which doubled the chromosome number allowing reproductive pairing and division to occur. With normal pairing and division, triticale could be reproduced through subsequent generations. Once a fertile hybrid of triticale was produced, it became possible to create new combinations between wheat and rye and to intercross triticale with various common wheat. Triticale became a new crop plant, similar to, but distinct from common wheat, rye, and other cereal grains in breeding, seed production, and use. Triticale is self-pollinating (similar to common wheat) and not cross-pollinating (like rye). Once created and reproduced, a triticale does not revert or break-down to its original wheat and rye components.

Breeding programs begun in the 1950's and 1960's in Poland, Mexico, Canada, and the U.S. pioneered the success of today's modern triticale varieties. Modern breeding programs concentrate on developing varieties with improved animal feed and fodder for production under diverse environmental conditions, as well as attempts to breed triticale varieties more suitable for human consumption. Triticale is managed like common wheat, though it requires fewer inputs such as water, fertilizer, and pesticides.

Most of the triticale grown in the United States is used for feed grain and forage for swine, dairy cattle, and poultry. Triticale competes with other cereal grains, primarily common wheat and oats, for these forage markets. These markets in the U.S. are substantial. Annually in the U.S., over 18 million acres of cereal grains are planted for forage production. In the southern Central Plains alone, over 12 million acres of common wheat are used for pasture for grazing on average each year. Cereal silage and hay are important in the major dairy producing regions, and cereal hay is a popular forage for horses.

Compared to common wheat and oats, triticale has important advantages for forage production in terms of yield, production costs, and tolerance to pests, drought, low fertility, mineral toxicities, and heavy grazing (National Research Council: A Promising Addition to the World's Cereal Grains, National Academy Press, Washington, D.C. 1989). Triticale is generally superior to all classes of common wheat for pasture, silage, hay, and for grain used for feed. Triticales, like common wheat, have either a winter or spring growth habit, but vary significantly in plant height, tend to tiller less, and have a larger inflorescence when compared with common wheat. The majority of triticale cultivars have prominent awns, which sometimes cause problems in pastures or in hay. Recent releases are awnless and have increased its potential use as forage.

Common wheat and triticale have many similarities in their pattern of plant development and morphology. The flower heads or spikes, develop at the top of the main stems and secondary stems called tillers, which are analogous to branches. An individual plant usually has a main stem and multiple tillers, the number of which depends on plant density, soil moisture, nutrient supply, pest damage, seeding date, and temperature, as well as the genetics of the plant. Typically, two to four tillers per plant will develop to the point of developing a head. Each head at the top of the stem consists of multiple spikelets, each of which consists of multiple florets that produce pollen, ovules, and ultimately, kernels.

World triticale production has increased nearly 50% from 1991 to 2001 (United Nations—FAOSTAT). According to the United Nations Food and Agriculture Organization, it is estimated that over 10 million acres and an average of 3,021 lb/acre were produced worldwide in 2004. Major producers include China, Poland, Germany, France, and Australia. Estimates in the United States alone approached 1 million acres in 2004.

Currently, most of the triticale that is grown in the United States is used for forage, and it is difficult to obtain statistical data on yield because it is not differentiated from wheat forage and other small grain forage in USDA reports. Most of the triticale acreage in the United States is in the Southern Plains as an annual cool-season pasture, while the remaining acreage is grown in either the Northern dairy states as forage, in the Southeast for silage, and in the Intermountain West for beef pasture.

Triticale has many benefits to offer crop producers, livestock feeders, and for commercial use in soft-dough mixtures. Its major strength is its versatility: it can be used for grazing, silage, feed, cover crops, straw, and even human consumption. Additionally, production of triticale provides environmental benefits such as erosion control and improved nutrient cycling through crop rotation. Thus, because of its considerable benefits, significant plant breeding effort has been directed towards breeding triticale.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single cultivar an improved combination of desirable traits from the parental germplasm. In triticale, the important traits include increased yield and quality, resistance to diseases and insects, resistance to drought and heat, and improved agronomic traits.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to popular cultivars in environments representative of the commercial target area(s) for three or more years. The best lines having superiority over the popular cultivars are candidates to become new commercial cultivars. Those lines still deficient in a few traits are discarded or utilized as parents to produce new populations for further selection.

These processes, which lead to the final step of marketing and distribution, usually take from seven to twelve years from the time the first cross is made. Therefore, development of new cultivars is a time-consuming process that requires precise forward planning, efficient use of resources, and a minimum of changes in direction.

A most difficult task is the identification of individuals that are genetically superior because, for most traits the true genotypic value is masked by other confounding plant traits or environmental factors. One method of identifying a superior plant is to observe its performance relative to other experimental lines and widely grown standard cultivars. For many traits a single observation is inconclusive, and replicated observations over time and space are required to provide a good estimate of a line's genetic worth.

The goal of a commercial triticale breeding program is to develop new, unique and superior triticale cultivars. The breeder initially selects and crosses two or more parental lines, followed by generation advancement and selection, thus producing many new genetic combinations. The breeder can theoretically generate billions of different genetic combinations via this procedure. The breeder has no direct control over which genetic combinations will arise in the limited population size which is grown. Therefore, two breeders will never develop the same line having the same traits.

Each year, the plant breeder selects the germplasm to advance to the next generation. This germplasm is grown under unique and different geographical, climatic and soil conditions, and further selections are then made, during and at the end of the growing season. The lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce, with any reasonable likelihood, the same cultivar twice by using the exact same original parents and the same selection techniques. This unpredictability results in the expenditure of large amounts of research moneys to develop superior new triticale cultivars.

Pureline cultivars of triticale are commonly bred by hybridization of two or more parents followed by selection. The complexity of inheritance, the breeding objectives and the available resources influence the breeding method. Pedigree breeding, recurrent selection breeding and backcross breeding are breeding methods commonly used in self pollinated crops such as triticale. These methods refer to the manner in which breeding pools or populations are made in order to combine desirable traits from two or more cultivars or various broad-based sources. The procedures commonly used for selection of desirable individuals or populations of individuals are called mass selection, plant-to-row selection and single seed descent or modified single seed descent. One, or a combination of these selection methods, can be used in the development of a cultivar from a breeding population.

Pedigree breeding is primarily used to combine favorable genes into a totally new cultivar that is different in many traits than either parent used in the original cross. It is commonly used for the improvement of self-pollinating crops. Two parents which possess favorable, complementary traits are crossed to produce an $F_1$ (filial generation 1). An $F_2$ population is produced by selfing $F_1$ plants. Selection of desirable individual plants may begin as early as the $F_2$ generation wherein maximum gene segregation occurs. Individual plant selection can occur for one or more generations. Successively, seed from each selected plant can be planted in individual, identified rows or hills, known as progeny rows or progeny hills, to evaluate the line and to increase the seed quantity, or, to further select individual plants. Once a progeny row or progeny hill is selected as having desirable traits it becomes what is known as a breeding line that is specifically identifiable from other breeding lines that were derived from the same original population. At an advanced generation (i.e., $F_5$ or higher) seed of individual lines are evaluated in replicated testing. At an advanced stage the best lines or a mixture of phenotypically similar lines from the same original cross are tested for potential release as new cultivars.

The single seed descent procedure in the strict sense refers to planting a segregating population, harvesting one seed from every plant, and combining these seeds into a bulk which is planted the next generation. When the population has been advanced to the desired level of inbreeding, the plants from which lines are derived will each trace to different $F_2$ individuals. Primary advantages of the seed descent procedures are to delay selection until a high level of homozygosity (e.g., lack of gene segregation) is achieved in individual plants, and to move through these early generations quickly, usually through using off-season nurseries.

Selection for desirable traits can occur at any segregating generation ($F_2$ and above). Selection pressure is exerted on a population by growing the population in an environment where the desired trait is maximally expressed and the individuals or lines possessing the trait can be identified. For instance, selection can occur for disease resistance when the plants or lines are grown in natural or artificially-induced disease environments, and the breeder selects only those individuals having little or no disease and are thus assumed to be resistant.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max* L. Merr.) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD and three classical markers and four isozyme loci. See also, Shoemaker, R. C., RFLP Map of Soybean, p 299-309, in Phillips, R. L. and Vasil, I. K. (eds.) DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Starch Gel Electrophoresis, Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. For example, molecular markers are used in soybean breeding for selection of the trait of resistance to soybean cyst nematode, see U.S. Pat. No. 6,162,967. The markers can also be used to select toward the genome of the recurrent parent and against the markers of the donor parent. Using this procedure can attempt to minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection. Molecular markers may also be used to identify and exclude certain sources of germplasm as parental varieties or ancestors of a plant by providing a means of tracking genetic profiles through crosses as discussed more fully hereinafter.

Mutation breeding is another method of introducing new traits into triticale varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogues like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in "Principles of Cultivar Development" by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Allard, 1960; Simmonds, 1979; Sneep, et al. 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, and the grower, processor and consumer; for special advertising and marketing and commercial production practices, and new product utilization. The testing preceding the release of a new cultivar should take into consideration research and development costs as well as technical superiority of the final cultivar. For seed-propagated cultivars, it must be feasible to produce seed easily and economically.

Triticale is an important and valuable field crop. Thus, a continuing goal of triticale plant breeders is to develop stable, high yielding triticale cultivars that are agronomically sound. The reasons for this goal are obviously to maximize yield and the quality of the final product for forage, silage, and human consumption. To accomplish this goal, the triticale breeder must select and develop plants that have the traits that result in superior cultivars.

The development of new triticale cultivars requires the evaluation and selection of parents and the crossing of these parents. The lack of predictable success of a given cross requires that a breeder, in any given year, make several crosses with the same or different breeding objectives.

The crossed or hybrid seed is produced by manual crosses between selected parents. Floral buds of the parent that is to be the female are emasculated prior to the opening of the flower by manual removal of the male anthers. At flowering, the pollen from flowers of the parent plants designated as male, are manually placed on the stigma of the previous emasculated flower. Seed developed from the cross is known as first generation ($F_1$) hybrid seed. Planting of this seed produces $F_1$ hybrid plants of which half their genetic component is from the female parent and half from the male parent. Segregation of genes begins at meiosis thus producing second generation ($F_2$) seed. Assuming multiple genetic differences between the original parents, each $F_2$ seed has a unique combination of genes.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

The present invention relates to a triticale seed, a triticale plant, a triticale cultivar and a method for producing a triticale plant.

The present invention further relates to a method of producing triticale seeds and plants by crossing a plant of the instant invention with another triticale plant.

This invention further relates to the seeds of triticale cultivar 97TV38011, to the plants of triticale cultivar 97TV38011 and to methods for producing a triticale plant produced by crossing the triticale 97TV38011 with itself or another triticale cultivar. Thus, any such methods using the triticale cultivar 97TV38011 are part of this invention, including selfing, backcrosses, hybrid production, crosses to populations, and the like.

In another aspect, the present invention provides for single trait converted plants of 97TV38011. The single transferred trait may preferably be a dominant or recessive allele. Preferably, the single transferred trait will confer such traits as herbicide resistance, insect resistance, resistance for bacterial, fungal, or viral disease, male fertility, male sterility, and industrial usage. The single trait may be a naturally occurring triticale gene or a transgene introduced through genetic engineering techniques.

In another aspect, the present invention provides regenerable cells for use in tissue culture of triticale plant 97TV38011. The tissue culture will preferably be capable of regenerating plants having the physiological and morphological characteristics of the foregoing triticale plant, and of regenerating plants having substantially the same genotype as the foregoing triticale plant. Preferably, the regenerable cells in such tissue cultures will be embryos, protoplasts, meristematic cells, callus, plant clumps, pollen, ovules, pericarp, seeds, flowers, florets, heads, spikes, leaves, roots, root tips, anthers, stems, and the like. Still further, the present invention provides triticale plants regenerated from the tissue cultures of the invention.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Allele. Allele is any of one or more alternative forms of a gene, all of which alleles relate to one trait or characteristic. In a diploid cell or organism, the two alleles of a given gene occupy corresponding loci on a pair of homologous chromosomes.

Awn. Awn is intended to mean the elongated needle-like appendages on the flower and seed-bearing "head" at the top of the cereal grain plant (e.g., triticale, common wheat, rye). These awns are attached to the lemmas. Lemmas enclose the stamen and the stigma as part of the florets. These florets are grouped in spikelets, which in turn together comprise the head.

Backcrossing. Backcrossing is a process in which a breeder repeatedly crosses hybrid progeny back to one of the parents, for example, a first generation hybrid $F_1$ with one of the parental genotypes of the $F_1$ hybrid.

Disease Resistance. As used herein, the term "disease resistance" is defined as the ability of plants to restrict the activities of a specified pest, such as an insect, fungus, virus, or bacterial.

Disease Tolerance. As used herein, the term "disease tolerance" is defined as the ability of plants to endure a specified pest (such as an insect, fungus, virus or bacteria) or an adverse environmental condition and still perform and produce in spite of this disorder.

Essentially all of the physiological and morphological characteristics. A plant having essentially all of the physiological and morphological characteristics means a plant having the physiological and morphological characteristics of the recurrent parent, except for the characteristics derived from the converted trait.

Head. As used herein, the term "head" refers to a group of spikelets at the top of one plant stem. The term "spike" also refers to the head of a plant located at the top of one plant stem.

Kernel Weight. As used herein, the term "kernel weight" refers to the weight of individual kernels (also called seeds), often reported as the weight of one thousand kernels or "1000 Kernel Weight".

Lodging. As used herein, the term "lodging" refers to the bending or breakage of the plant stem, or the tilting over of the plant, which complicates harvest and can diminish the value of the harvested product.

Maturity. As used herein, the term "maturity" refers to the stage of plant growth at which the development of the kernels is complete.

Test Weight. As used herein, the term "test weight" is a measure of density that refers to the weight in pounds of the amount of kernels contained in a bushel unit of volume.

Plant Height (Hgt). As used herein, the term "plant height" is defined as the average height in inches or centimeters of a group of plants.

Stripe Rust. A disease of triticale, common wheat, durum wheat, and barley characterized by elongated rows of yellow spores on the affected parts, caused by a rust fungus, *Puccinia striiformis*.

Single Trait Converted (Conversion). Single trait converted (conversion) plant refers to plants which are developed by a plant breeding technique called backcrossing or via genetic engineering wherein essentially all of the desired morphological and physiological characteristics of a variety are recovered in addition to the single trait transferred into the variety via the backcrossing technique or via genetic engineering.

DETAILED DESCRIPTION OF THE INVENTION

Triticale 97TV38011 is derived from a cross made with germplasm obtained from the International Maize and Wheat Improvement Center, with seed purification beginning in 1998.

The variety has shown uniformity and stability, as described in the following variety description information. The variety can have some taller variants at a frequency of no more than 0.5%. It has been self-pollinated a sufficient number of generations with careful attention to uniformity of plant type. The line has been increased with continued observation for uniformity. Triticale 97TV38011 is adapted to the Central Valley of California.

TABLE 1

VARIETY DESCRIPTION INFORMATION

| | |
|---|---|
| Species: | *Triticale hexaploide* L. |
| General: | Growth habit: Spring |
| | Juvenile plant growth: Erect |
| | Photoperiod: Insensitive |
| Ploidy: | Type: Hexaploid |
| | 2n chromosome number: 42 |
| Height: | Type: Normal |
| | Cm above the soil: 104 |
| Plant Color at Boot Stage: | Blue-green |
| Stem: | Anthocyanin: Absent |
| | Neck pubescence: Prominent |
| | Shape of neck: Wavy |
| Leaves: | Flag leaf: Twisted |
| | Waxy bloom on leaf at boot: Present |

TABLE 1-continued

VARIETY DESCRIPTION INFORMATION

| | |
|---|---|
| | Leaf carriage: Upright |
| | Length: 29 cm |
| | Width: 15 cm |
| | Auricle color: Colorless |
| Head: | Density: Middense |
| | Shape: Fusiform |
| | Awnedness: Awned |
| | Awn color: Yellow |
| | Length: 12 cm |
| | Width: 1.6 cm |
| Glumes at Maturity: | Pubescence: Pubescent |
| | Color: Tan |
| | Length: Long |
| | Width: Narrow |
| | Shoulder: Square |
| | Beak: Obtuse |
| Seed: | Shape: Elliptical |
| | Smoothness: Slightly wrinkled |
| | Brush area: Midsize |

TABLE 1-continued

VARIETY DESCRIPTION INFORMATION

| | |
|---|---|
| | Brush length: Mid-long |
| | Color: Amber |
| | Weight (grams/1,000 seeds): 44 |
| Diseases: | Stripe Rust: Resistant |

In addition to the morphological characteristics and disease and pest resistance described above, triticale cultivar 97TV38011 has the following characteristics, for which there are significant differences from the comparison varieties, TRITICAL 105, TRITICAL 111, and TRITICAL 96, at the 5% level of probability or less. As shown in Table 2 below, comparative data was taken at the University of California trial in 2004. Column one shows the variety, column two shows the test weight in pounds per bushel, column three shows the kernel weight as grams per 1000 seeds, column four shows the head development taken in days after March 1, column five shows the maturity date taken as days after March 1, column six shows the plant height in inches, column seven shows the Stripe Rust reaction, and column eight shows the lodging reaction at harvest. Triticale cultivar 97TV38011 is similar to TRITICAL 105 for test weight and maturity date but has numerous differences including kernel weight and lodging reaction.

TABLE 2

| Variety | Test Weight | Kernel Weight | Head | Maturity | Plant Height | Stripe Rust* | Lodging at Harvest* |
|---|---|---|---|---|---|---|---|
| Triticale 97TV38011 | 58.6 | 42.9 | 86 | 140 | 39.3 | 1.4 | 1.5 |
| TRITICAL 105 | 58.2 | 47.4 | 89 | 140 | 41.6 | 1.0 | 2.4 |
| TRITICAL 111 | 55.8 | 47.0 | 88 | 140 | 40.6 | 1.0 | 1.2 |
| TRITICAL 96 | 57.7 | 42.4 | 84 | 138 | 34.8 | 3.4 | 1.0 |

*Stripe Rust and Lodging reactions are given on a scale of 1-5, where 1 = 0-3%, 2 = 4-14%, 3 = 15-29%, 4 = 30-49%, and 5 = 50-69%.

This invention is also directed to methods for producing a triticale plant by crossing a first parent triticale plant with a second parent triticale plant, wherein the first or second triticale plant is the triticale plant from the cultivar 97TV38011. Further, both the first and second parent triticale plants may be the cultivar 97TV38011 (e.g., self-pollination). Further, the first or second parent may be a common wheat cultivar. Therefore, any methods using the cultivar 97TV38011 are part of this invention: selfing, backcrosses, hybrid breeding, and crosses to populations. Any plants produced using cultivar 97TV38011 as a parent are within the scope of this invention. As used herein, the term "plant" includes plant cells, plant protoplasts, plant cells of tissue culture from which triticale plants can be regenerated, plant calli, plant clumps, and plant cells that are intact in plants or parts of plants, such as pollen, flowers, embryos, ovules, seeds, leaves, stems, roots, anthers and the like. Thus, another aspect of this invention is to provide for cells which upon growth and differentiation produce a cultivar having essentially all of the physiological and morphological characteristics of 97TV38011.

The present invention contemplates a triticale plant regenerated from a tissue culture of a cultivar (e.g., 97TV38011) or hybrid plant of the present invention. As is well known in the art, tissue culture of triticale can be used for the in vitro regeneration of a triticale plant. Tissue culture of various tissues of plants and regeneration of plants therefrom is well known and widely published.

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed cultivar.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed triticale plants, using transformation methods as described below to incorporate transgenes into the genetic material of the triticale plant(s).

Expression Vectors for Triticale Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII), which, when under the control of plant regulatory signals confers resistance to kanamycin. Fraley et al., *Proc. Natl. Acad. Sci. U.S.A.,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988), Jones et al., *Mol. Gen. Genet,* 210:86 (1987), Svab et al., *Plant Mol. Biol.* 14:197 (1990) Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Other selectable marker genes for plant transformation that are not of bacterial origin include, for example, mouse dihydrofolate reductase, plant 5-enolpyruvyl -shikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984).

In vivo methods for visualizing GUS activity that do not require destruction of plant tissue are available. Molecular Probes publication 2908, Imagene Green, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for Triticale Transformation: Promoters

Genes included in expression vectors must be driven by a nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in triticale. Optionally, the inducible promoter is operably linked to a nucleotide sequence encoding a signal sequence which is operably linked to a gene for expression in triticale. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Mett et al., *PNAS* 90:4567-4571 (1993)); ln2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in triticale or the constitutive promoter is operably linked to a nucleotide sequence encoding a signal sequence which is operably linked to a gene for expression in triticale.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters—A tissue-specific promoter is operably linked to a gene for expression in triticale. Optionally, the tissue-specific promoter is operably linked to a nucleotide sequence encoding a signal sequence which is operably linked to a gene for expression in triticale. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter—such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is a triticale plant. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A gene conferring resistance to a pest, such as nematodes. See e.g., PCT Application WO 96/30517; PCT Application WO 93/19181.

C. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

D. A lectin. See, for example, the disclosure by Van Damme et al., *Plant Molec. Biol.* 24:25 (1994), who disclose the nucleotide sequences of several *Clivia miniata* mannose-binding lectin genes.

E. A vitamin-binding protein such as avidin. See PCT application US93/06487. The application teaches the use of avidin and avidin homologues as larvicides against insect pests.

F. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor) and U.S. Pat. No. 5,494,813 (Hepher and Atkinson, issued Feb. 27, 1996).

G. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

H. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

I. An insect-specific venom produced in nature by a snake, a wasp, etc. For example, see Pang et al., *Gene* 116:165 (1992), for disclosure of heterologous expression in plants of a gene coding for a scorpion insectotoxic peptide.

J. An enzyme responsible for a hyper-accumulation of a monoterpene, a sesquiterpene, a steroid, a hydroxamic acid, a phenylpropanoid derivative or another non-protein molecule with insecticidal activity.

K. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

L. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

M. A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance).

N. A membrane permease, a channel former or a channel blocker. For example, see the disclosure of Jaynes et al., *Plant Sci* 89:43 (1993), of heterologous expression of a cecropin-β lytic peptide analog to render transgenic tobacco plants resistant to *Pseudomonas solanacearum*.

O. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

P. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

Q. A virus-specific antibody. See, for example, Taviadoraki et al., *Nature* 366:469 (1993), who show that transgenic plants expressing recombinant antibody genes are protected from virus attack.

R. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

S. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989), describe the production of transgenic plants that express chimeric bar genes coding for PAT activity. Exemplary of genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibila et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419,1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Nat. Acad. Sci. U.S.A.* 89:2624 (1992).

B. Decreased phytate content—1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene. 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus lichenifonnis* α-amylase), Elliot et al., *Plant Molec. Biol.* 21:515 (1993) (nucleotide sequences of tomato invertase genes), SØgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

D. Elevated oleic acid via FAD-2 gene modification and/or decreased linolenic acid via FAD-3 gene modification. See U.S. Pat. Nos. 6,063,947; 6,323,392; and international publication WO 93/11245.

E. The content of high-molecular weight gluten subunits (HMS-GS). Genomic clones have been isolated for different subunits (Anderson et al., In Proceedings of the 7th International Wheat Genetics Symposium, IPR, pp. 699-704, 1988; Shewry et al. In Oxford Surveys of Plant Molecular and Cell Biology, pp. 163-219, 1989; Shewry et al. *Journal of Cereal Sci.* 15:105-120, 1992). Blechl et al. (Journal of *Plant Phys.* 152 (6): 703-707, 1998) have transformed wheat with genes that encode a modified HMW-GS. See also U.S. Pat. Nos. 5,650,558; 5,914,450; 5,985,352; 6,174,725; and 6,252,134, which are incorporated herein by reference for this purpose.

4. Genes that Control Male Sterility

A. Introduction of a deacetylase gene under the control of a tapetum-specific promoter and with the application of the chemical N-Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for Triticale Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,563,055 (Townsend and Thomas), issued Oct. 8, 1996.

B. Direct Gene Transfer—Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). See also U.S. Pat. No. 5,015,580 (Christou, et al.), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine has also been reported. Hain et al., *Mol. Gen. Genet.* 199:161 (1985) and Draper et al., *Plant Cell Physiol.* 23:451 (1982). Electroporation of protoplasts and whole cells and tissues has also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of triticale target tissues, expression of the above-described selectable marker genes allows for preferential selection of transformed cells, tissues and/or plants, using regeneration and selection methods now well known in the art.

The foregoing methods for transformation would typically be used for producing a transgenic variety. The transgenic variety could then be crossed, with another (nontransformed or transformed) variety, in order to produce a new transgenic variety. Alternatively, a genetic trait which has been engineered into a particular triticale cultivar using the foregoing transformation techniques could be moved into another cultivar using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties which do not contain that gene. As used herein, "crossing" can refer to a simple X by Y cross, or the process of backcrossing, depending on the context.

Single-Gene Conversion

When the term "triticale plant" is used in the context of the present invention, this also includes any single gene conversions of that variety. The term "single gene converted plant" as used herein refers to those triticale plants which are developed by a plant breeding technique called backcrossing wherein essentially all of the desired morphological and physiological characteristics of a variety are recovered in addition to the single gene transferred into the variety via the backcrossing technique. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9 or more times to the recurrent parent. The parental triticale plant which contributes the gene for the desired characteristic is termed the "nonrecurrent" or "donor parent". This terminology refers to the fact that the nonrecurrent parent is used one time in the backcross protocol and therefore does not recur. The parental triticale plant to which the gene or genes from the nonrecurrent parent are transferred is known as the recurrent parent as it is used for several rounds in the backcrossing protocol (Poehiman & Sleper, 1994; Fehr, 1987). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a triticale plant is obtained wherein essentially all of the desired morphological and physiological characteristics of the recurrent parent are recovered in the converted plant, in addition to the single transferred gene from the nonrecurrent parent, as determined at the 5% significance level when grown in the same environmental conditions.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Several of these single gene traits are described in U.S. Pat. Nos. 5,959,185, 5,973,234 and 5,977,445, the disclosures of which are specifically hereby incorporated by reference.

Further reproduction of the variety can occur by tissue culture and regeneration. Tissue culture of various tissues of triticale and regeneration of plants therefrom is well known and widely published. For example, reference may be had to Komatsuda, T. et al., *Crop Sci.* 31:333-337 (1991); Stephens, P. A., et al., *Theor. Appl. Genet* 82:633-635 (1991); Komatsuda, T. et al., *Plant Cell, Tissue and Organ Culture,* 28:103-113 (1992); Dhir, S. et al. *Plant Cell Reports* 11:285-289 (1992); Pandey, P. et al., *Japan J. Breed.* 42:1-5 (1992); and Shetty, K., et al., *Plant Science* 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce triticale plants having the physiological and morphological characteristics of triticale cultivar 97TV38011.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, ovules, pericarp, flowers, florets, heads, spikes, seeds, leaves, stems, roots, root tips, anthers, awns, stems, and the like. Means for preparing and maintaining plant tissue culture are well known in the art. By way of example, a tissue culture comprising organs has been used to produce regenerated plants. U.S. Pat. Nos. 5,959, 185, 5,973,234 and 5,977,445, describe certain techniques.

This invention also is directed to methods for producing a triticale plant by crossing a first parent triticale plant with a second parent triticale plant wherein the first or second parent triticale plant is a triticale plant of the cultivar 97TV38011. Further, both first and second parent triticale plants can come from the triticale cultivar 97TV38011. Thus, any such methods using the triticale cultivar 97TV38011 are part of this invention: selfing, backcrosses, hybrid production, crosses to populations, and the like. All plants produced using triticale cultivar 97TV38011 as a parent are within the scope of this invention, including those developed from varieties derived from triticale cultivar 97TV38011. Advantageously, the triticale cultivar could be used in crosses with other, different, triticale plants to produce first generation ($F_1$) triticale hybrid seeds and plants with superior characteristics. The cultivar of the invention can also be used for transformation where exogenous genes are introduced and expressed by the cultivar of the invention. Genetic variants created either through traditional breeding methods using cultivar 97TV38011 or through transformation of 97TV38011 by any of a number of protocols known to those of skill in the art are intended to be within the scope of this invention.

The following describes breeding methods that may be used with cultivar 97TV38011 in the development of further triticale plants. One such embodiment is a method for developing an 97TV38011 progeny triticale plant in a triticale plant breeding program comprising: obtaining the triticale plant, or a part thereof, of cultivar 97TV38011 utilizing said plant or plant part as a source of breeding material and selecting an 97TV38011 progeny plant with molecular markers in common with 97TV38011 and/or with morphological and/or physiological characteristics selected from the characteristics listed in Tables 1 and 2. Breeding steps that may be used in the triticale plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of cultivar 97TV38011 progeny triticale plants, comprising crossing cultivar 97TV38011 with another triticale plant, thereby producing a population of triticale plants, which, on average, derive 50% of their alleles from cultivar 97TV38011. A plant of this population may be selected and repeatedly selfed or sibbed with a triticale cultivar resulting from these successive filial generations. One embodiment of this invention is the triticale cultivar produced by this method and that has obtained at least 50% of its alleles from cultivar 97TV38011.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes triticale cultivar 97TV38011 progeny triticale plants comprising a combination of at least two 97TV38011 traits selected from the group consisting of those listed in Tables 1 and 2 or the 97TV38011 combination of traits listed in the Summary of the Invention, so that said progeny triticale plant is not significantly different for said traits than triticale cultivar 97TV38011 as determined at the 5% significance level when grown in the same environment. Using techniques described herein, molecular markers may be used to identify said progeny plant as a 97TV38011 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of cultivar 97TV38011 may also be characterized through their filial relationship with triticale cultivar 97TV38011, as for example, being within a certain number of breeding crosses of triticale cultivar 97TV38011. A breeding cross is a cross made to introduce new genetics into the progeny, and is distinguished from a cross, such as a self or a sib cross, made to select among existing genetic alleles. The lower the number of breeding crosses in the pedigree, the closer the relationship between triticale cultivar 97TV38011 and its progeny. For example, progeny produced by the methods described herein may be within 1, 2, 3, 4 or 5 breeding crosses of triticale cultivar 97TV38011.

As used herein, the term "plant" includes plant cells, plant protoplasts, plant cell tissue cultures from which triticale plants can be regenerated, plant calli, plant clumps, and plant cells that are intact in plants or parts of plants, such as embryos, pollen, awns, ovules, pericarp, seed, flowers, florets, heads, spikes, leaves, roots, root tips, anthers, stems, and the like.

TABLES

As shown in Table 3 below, triticale cultivar 97TV38011 is compared to various commercial triticale cultivars for average yield in pounds/acre in a University of California regional trial in 2004 for which there are significant differences from the comparison varieties at the 5% significance level. The data are averages taken over seven test sites. Column one shows the variety name and column two shows the average yield in pounds/acre.

TABLE 3

| Variety | Average Pounds/Acre |
| --- | --- |
| Triticale Cultivar 97TV38011 | 6456 |
| TRICAL 116 | 5301 |
| RSI 98TV60147 | 5329 |
| TRICAL 96 | 5113 |
| TRICAL 111 | 5103 |
| TRICAL 105 | 4913 |

As shown in Table 4 below, triticale cultivar 97TV38011 is compared to various commercial triticale cultivars for average yield in pounds/acre in a University of California regional trial in 2005 for which there are significant differences from the comparison varieties at the 5% significance level. The data are averages taken over seven test sites. Column one shows the variety name and column two shows the average yield in pounds/acre.

TABLE 4

| Variety | Average Pounds/Acre |
| --- | --- |
| Triticale Cultivar 97TV38011 | 6835 |
| TRICAL 116 | 5854 |
| RSI 98TV60147 | 6103 |
| TRICAL 96 | 6075 |
| TRICAL 105 | 5102 |

DEPOSIT INFORMATION

A deposit of the Resource Seeds, Inc. proprietary triticale cultivar 97TV38011 disclosed above and recited in the appended claims has been made with the American Type Culture Collection (ATCC). 10801 University Boulevard, Manassas, Va. 20110. The date of deposit was Jun. 20, 2007. The deposit of 2,500 seeds was taken from the same deposit maintained by Resource Seeds, Inc. since prior to the filing date of this application. All restrictions upon the deposit have been removed, and the deposit is intended to meet all of the requirements of 37 C.F.R. §1.801-1.809. The ATCC accession number is PTA-8488 The deposit will be maintained in the depository for a period of 30 years, or 5 years after the last request, or for the effective life of the patent, whichever is lonqer, and will be replaced as necessary durinq that period.

What is claimed is:

1. A seed of triticale cultivar 97TV38011, wherein a representative sample of seed of said cultivar was deposited under ATCC Accession No. PTA-8488.

2. A triticale plant, or a part thereof, produced by growing the seed of claim 1.

3. A tissue culture of cells produced from the plant of claim 2, wherein said cells of the tissue culture are produced from a plant part selected from the group consisting of heads, awns, leaves, pollen, embryos, cotyledons, hypocotyls, meristematic cells, roots, root tips, pistils, anthers, flowers, stems, and calli.

4. A protoplast produced from the plant of claim 2.

5. A protoplast produced from the tissue culture of claim 3.

6. A triticale plant regenerated from the tissue culture of claim 3, wherein the plant has all of the morphological and physiological characteristics of cultivar 97TV38011 wherein a representative sample of seed was deposited under ATCC Accession No. PTA-8488.

7. A method for producing an $F_1$ hybrid triticale seed, wherein the method comprises crossing the plant of claim 2 with a different triticale plant and harvesting the resultant $F_1$ hybrid triticale seed.

8. A hybrid triticale seed produced by the method of claim 7.

9. A hybrid triticale plant, or a part thereof, produced by growing said hybrid seed of claim 8.

10. A method of producing an herbicide resistant triticale plant wherein the method comprises transforming the triticale plant of claim 2 with a transgene wherein the transgene confers resistance to an herbicide selected from the group consisting of imidazolinone, sulfonylurea, glyphosate, glufosinate, L-phosphinothricin, triazine and benzonitrile.

11. An herbicide resistant triticale plant produced by the method of claim 10.

12. A method of producing an insect resistant triticale plant wherein the method comprises transforming the triticale plant of claim 2 with a transgene that confers insect resistance.

13. An insect resistant triticale plant produced by the method of claim 12.

14. The triticale plant of claim 13, wherein the transgene encodes a *Bacillus thuringiensis* endotoxin.

15. A method of producing a disease resistant triticale plant wherein the method comprises transforming the triticale plant of claim 2 with a transgene that confers disease resistance.

16. A disease resistant triticale plant produced by the method of claim 15.

17. A method of producing a triticale plant with modified fatty acid metabolism, modified carbohydrate metabolism wherein the method comprises transforming the triticale plant of claim 2 with a transgene encoding a protein selected from the group consisting of phytase, fructosyltransferase, levansucrase, α-amylase, invertase and starch branching enzyme or encoding an antisense of stearyl-ACP desaturase.

18. A triticale plant having modified fatty acid metabolism or modified carbohydrate metabolism produced by the method of claim 17.

19. A method of introducing a desired trait into triticale cultivar 97TV38011 wherein the method comprises:
(a) crossing a 97TV38011 plant, wherein a representative sample of seed was deposited under ATCC Accession No. PTA-8488, with a plant of another triticale cultivar that comprises a desired trait to produce progeny plants wherein the desired trait is selected from the group consisting of male sterility, herbicide resistance, insect resistance, modified fatty acid metabolism, modified carbohydrate metabolism, modified phytic metabolism, modified waxy starch content, modified gluten content and resistance to bacterial disease, fungal disease or viral disease;

(b) selecting one or more progeny plants that have the desired trait to produce selected progeny plants;

(c) crossing the selected progeny plants with the 97TV38011 plants to produce backcross progeny plants;

(d) selecting for backcross progeny plants that have the desired trait and all of the physiological and morphological characteristics of triticale cultivar 97TV38011 listed in Table 1 to produce selected backcross progeny plants; and (e) repeating steps (c) and (d) three or more times in succession to produce selected fourth or higher backcross progeny plants that comprise the desired trait and all of the physiological and morphological characteristics of triticale cultivar 97TV38011 listed in Table 1.

20. A triticale plant produced by the method of claim 19, wherein the plant has the desired trait and all of the physiological and morphological characteristics of triticale cultivar 97TV38011 listed in Table 1.

21. The triticale plant of claim 20, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

22. The triticale plant of claim 20, wherein the desired trait is insect resistance and the insect resistance is conferred by a transgene encoding a *Bacillus thuringiensis* endotoxin.

23. The triticale plant of claim 20, wherein the desired trait is modified fatty acid metabolism or modified carbohydrate metabolism and said desired trait is conferred by a nucleic acid encoding a protein selected from the group consisting of phytase, fructosyltransferase, levansucrase, α-amylase, invertase and starch branching enzyme or encoding an antisense of stearyl-ACP desaturase.

24. The triticale plant of claim 20, wherein the desired trait is male sterility and the trait is conferred by a cytoplasmic nucleic acid molecule that confers male sterility.

* * * * *